US012417850B2

(12) United States Patent
Valles Leon (10) Patent No.: US 12,417,850 B2
(45) Date of Patent: Sep. 16, 2025

(54) TELEHEALTH CONTROL SYSTEM AND METHOD

(71) Applicant: MDLIVE, Inc., Miramar, FL (US)

(72) Inventor: Nakort E. Valles Leon, Weston, FL (US)

(73) Assignee: MDLive, Inc., Miramar, FL (US)

( * ) Notice: Subject to any disclaimer, the term of this patent is extended or adjusted under 35 U.S.C. 154(b) by 544 days.

(21) Appl. No.: 17/748,170

(22) Filed: May 19, 2022

(65) Prior Publication Data
US 2022/0384060 A1 Dec. 1, 2022

Related U.S. Application Data

(60) Provisional application No. 63/193,874, filed on May 27, 2021.

(51) Int. Cl.
*G16H 80/00* (2018.01)
*G16H 40/20* (2018.01)

(52) U.S. Cl.
CPC ............ *G16H 80/00* (2018.01); *G16H 40/20* (2018.01)

(58) Field of Classification Search
CPC ......... G16H 80/00; G16H 40/20; G16H 40/67
See application file for complete search history.

(56) References Cited

U.S. PATENT DOCUMENTS

| | | | |
|---|---|---|---|
| 9,990,608 B2 | 6/2018 | Phillips | |
| 10,741,279 B2 | 8/2020 | Bullington | |
| 11,593,710 B1 * | 2/2023 | Snopek | G16H 20/10 |
| 2004/0204964 A1 | 10/2004 | Moore | |
| 2008/0303811 A1 | 12/2008 | Van Luchene | |
| 2013/0253339 A1 * | 9/2013 | Reyes | G06Q 10/06 600/549 |
| 2014/0019149 A1 | 1/2014 | Yu | |
| 2014/0180715 A1 | 6/2014 | Phillips | |
| 2014/0330579 A1 | 11/2014 | Cashman | |

(Continued)

OTHER PUBLICATIONS

Patient Self-Scheduling, Digital Patient Check In, Change Healthcare; https://www.changehealthcare.com/solutions/consumer-experience/patient-experience/virtual-front-desk; accessed as early as May 9, 2021.

(Continued)

*Primary Examiner* — Joshua B Blanchette
(74) *Attorney, Agent, or Firm* — The Small Patent Law Group (57) ABSTRACT

A telehealth control system and method examine a data structure to determine whether a patient having a waiting location in an order among several patients in a virtual waiting room for a virtual encounter with a healthcare provider has been waiting at least as long as a threshold time period. Responsive to determining that the patient has been waiting for at least as long as the threshold time period, the data structure is changed to indicate that the patient is locked out of the virtual waiting room while a scheduling system of the telehealth system attempts to schedule an upcoming virtual appointment involving the patient. Responsive to being unable to schedule the upcoming virtual appointment involving the patient, the data structure is changed to return the patient to the virtual waiting room without the patient losing the waiting location in the order of the virtual waiting room.

20 Claims, 7 Drawing Sheets

(56) References Cited

U.S. PATENT DOCUMENTS

| | | |
|---|---|---|
| 2014/0365240 A1 | 12/2014 | Canton |
| 2015/0127381 A1 | 5/2015 | Vo |
| 2017/0011179 A1* | 1/2017 | Arshad ................. H04L 63/102 |
| 2017/0011192 A1 | 1/2017 | Arshad |
| 2017/0228513 A1* | 8/2017 | Zhang .................... G06Q 10/06 |
| 2017/0235909 A1 | 8/2017 | Lozano |
| 2018/0240547 A1 | 8/2018 | Albert |

OTHER PUBLICATIONS

Qless, Take the "Wait" out of the Waiting Room, https://www.qless.com/healthcare-appointment-scheduling-app accessed as early as May 9, 2021.

Relatient; Virtual Waiting Room Solution: What it is, Why You Need it, and How to Create it—Relatient; https://www2.relatient.net/virtual-waiting-room-solution/; accessed as early as May 9, 2021.

\* cited by examiner

FIG. 1

1. Patient E0J4C27
2. Patient J0R5C27
3. Patient UI73IL6
4. Patient M0R5C26
5. Patient C1R1C25
6. Patient PF97K3JK
7. Patient Q78RR127
8. ...

*FIG. 2*

| ID | Entry | Lock Flag? |
| --- | --- | --- |
| Patient C1R1C25 | 44333, 0.440 | 0 |
| Patient E0J4C27 | 44332, 0.875 | 0 |
| Patient UI73IL6 | 44333, 0.427 | 0 |
| Patient J0R5C27 | 44332, 0.878 | 0 |
| Patient PF97K3JK | 44333, 0.610 | 0 |
| Patient Q78RR127 | 44333, 0.801 | 0 |
| Patient M0R5C26 | 44333, 0.431 | 0 |

┌─── 200
1. Patient E0J4C27
2. Patient J0R5C27
3. Patient UI73IL6
4. Patient M0R5C26
5. Patient C1R1C25
6. Patient PF97K3JK
7. Patient Q78RR127
8. ...

FIG. 4

| ID | Entry | Lock Flag? |
|---|---|---|
| Patient C1R1C25 | 44333, 0.440 | 1 |
| Patient E0J4C27 | 44332, 0.875 | 0 |
| Patient UI73IL6 | 44333, 0.427 | 0 |
| Patient J0R5C27 | 44332, 0.878 | 1 |
| Patient PF97K3JK | 44333, 0.610 | 0 |
| Patient Q78RR127 | 44333, 0.801 | 0 |
| Patient M0R5C26 | 44333, 0.431 | 0 |

1. Patient UI73IL6
2. Patient M0R5C26
3. Patient C1R1C25
4. Patient PF97K3JK
5. Patient Q78RR127
6. Patient PL80HH74
7. ...

FIG. 6

| ID | Entry | Lock Flag? |
|---|---|---|
| Patient C1R1C25 | 44333, 0.440 | 0 |
| Patient UI73IL6 | 44333, 0.427 | 0 |
| Patient Q78RR127 | 44333, 0.801 | 0 |
| Patient M0R5C26 | 44333, 0.431 | 0 |
| Patient PL80HH74 | 44333.0984 | 0 |
| Patient PF97K3JK | 44333, 0.610 | 0 |

TELEHEALTH CONTROL SYSTEM AND METHOD

CROSS-REFERENCE TO RELATED APPLICATIONS

This application claims priority to U.S. Provisional Application No. 63/193,874 (filed 27 May 2021), the entire disclosure of which is incorporated herein by reference.

BACKGROUND

Many different types of services can be provided via distributed or long-distance systems. For example, telehealth systems can provide health-related services and information via electronic information and telecommunication technologies. These systems can allow for long-distance provider and customer interaction via video conferencing and/or telephone calls. With respect to telehealth systems, healthcare providers may be able to be reached for consultations, medical appointments, etc., for a variety of medical issues.

With respect to telehealth systems, patients may seek an appointment with a healthcare provider via a remote encounter (e.g., a videoconference or teleconference). The patients may be placed into a virtual waiting room until a suitable and available healthcare provider is found. Once the suitable and available healthcare provider is found, the remote encounter may be established, and the patients may remotely interact with the providers to receive medical care, advice, and the like.

BRIEF DESCRIPTION

In one embodiment, a method includes examining a data structure stored in a database of a telehealth system to determine whether a patient having a waiting location in an order among several patients in a virtual waiting room for a virtual encounter with a healthcare provider has been waiting at least as long as a threshold time period and (responsive to determining that the patient has been waiting for at least as long as the threshold time period) changing the data structure stored in the database of the telehealth system to indicate that the patient is locked out of the virtual waiting room while a scheduling system of the telehealth system attempts to schedule an upcoming virtual appointment involving the patient. The method also includes (responsive to the scheduling system being unable to schedule the upcoming virtual appointment involving the patient) changing the data structure stored in the database of the telehealth system to return the patient to the virtual waiting room without the patient losing the waiting location in the order of the virtual waiting room. The use of the present methods and systems may operate to reduce conflicting resource usage. For example, the methods and systems can avoid, reduce, or prevent instances where a scheduling process and a real-time connection process executes or is performed on a same contact (e.g., a data structure dedicated to an individual patient) at the same time.

In one embodiment, a telehealth system includes one or more processors of a scheduling system configured to examine a data structure stored in a database of a telehealth system to determine whether a patient having a waiting location in an order among several patients in a virtual waiting room for a virtual encounter with a healthcare provider has been waiting at least as long as a threshold time period. The one or more processors are configured to change the data structure stored in the database of the telehealth system responsive to determining that the patient has been waiting for at least as long as the threshold time period. The one or more processors are configured to change the data structure to indicate that the patient is locked out of the virtual waiting room while a scheduling system of the telehealth system attempts to schedule an upcoming virtual appointment involving the patient. The one or more processors are configured to change the data structure stored in the database of the telehealth system to return the patient to the virtual waiting room without the patient losing the waiting location in the order of the virtual waiting room responsive to the scheduling system being unable to schedule the upcoming virtual appointment involving the patient.

In one embodiment, a method includes examining a data structure stored in a database of a telehealth system to determine whether a patient having a waiting location in an order among several patients in a virtual waiting room for a virtual encounter with a healthcare provider has been waiting at least as long as a threshold time period and, responsive to determining that the patient has been waiting for at least as long as the threshold time period, changing the data structure stored in the database of the telehealth system to indicate that the patient is locked out of the virtual waiting room while a scheduling system of the telehealth system attempts to schedule an upcoming virtual appointment involving the patient. The patient cannot be selected by the healthcare provider for the virtual encounter while the patient is locked out of the virtual waiting room. The method also includes, responsive to the scheduling system being unable to schedule the upcoming virtual appointment involving the patient, changing the data structure stored in the database of the telehealth system to return the patient to the virtual waiting room without the patient losing the waiting location in the order of the virtual waiting room. The data structure stored in the database of the telehealth system is changed to return the patient to the virtual waiting room without the patient losing the waiting location in the order of the virtual waiting room such that one or more subsequent patients that entered the virtual waiting room after the patient are behind the patient in the virtual waiting room.

DETAILED DESCRIPTION

Some telehealth systems may suffer from inefficiencies in initiating the encounters between the providers and patients. Patients waiting for a virtual or remote encounter with a provider may be placed into a queue when demand for encounters is greater and/or the supply of available providers is reduced. This queue can be referred to as a virtual waiting room as the patients are waiting for a remote interaction with a provider yet are not physically located in a room with other patients waiting for remote interactions with providers. Instead, the patients in the virtual waiting room, or queue, can be located elsewhere, such as their homes, offices, etc., while electronically linked to a database structure that maintains the queue.

The order in which patients are placed into the queue may be based on when the patients entered the virtual waiting room. For example, the telehealth queue control systems and methods described herein may record (e.g., in a database) the time and/or date when each patient enters a request into the telehealth system (e.g., via a patient device, such as a mobile phone, tablet computer, laptop computer, desktop computer, etc.) for a remote or virtual encounter with a provider. Patients waiting in the virtual waiting room can be ordered in a list or other structure based on when the patients entered into the virtual waiting room. For example, the queue control system can list the patients in a graphical user interface (GUI) for providers to select from (to initiate a remote encounter), with the patients listed in the order that the patients entered the virtual waiting room (e.g., the patients waiting longer are listed closer to the top of the list than patients that have not been waiting as long).

If a patient has been waiting longer than a designated wait time period, a scheduling system of the telehealth system can automatically reach out to the patient to schedule a date and/or time for a virtual encounter. For example, if a patient has been waiting in the virtual waiting room for more than thirty minutes (or another period of time), then the scheduling system may automatically call the patient, send an in-application notification on the patient's computing device, send an e-mail and/or text message to the patient, send a calendar invitation or appointment to an electronic calendar of the patient, or the like. The scheduling system can contact the patient and attempt to find a date and/or time that the patient and a provider are both available for the virtual encounter. If such a date and/or time is found, then the scheduling system can schedule the remote encounter between the patient and a provider. If a mutually agreeable date and/or time is not found, then the scheduling system can return the patient back to the virtual waiting room.

In one embodiment of the inventive subject matter described herein, the scheduling system can make the patient that is being contacted to schedule a remote encounter unavailable for selection by a provider in the virtual waiting room while the scheduling system is attempting to work with the patient to try and find a mutually agreeable date and/or time for the remote encounter. For example, the scheduling system can change a list, table, or other data structure in a database to include data (e.g., a lock key in a REDIS data structure store) that prevents the patient from being selected by a provider in the virtual waiting room. This can be implemented by removing the patient's name or other identifier from a list that providers select from to initiate the remote encounter, by changing the color of the patient's name or identifier in the list (e.g., graying out the patient's name or identifier), or otherwise indicating that the patient cannot be selected to initiate the remote encounter while the patient is corresponding with the scheduling system to schedule the remote encounter. This can prevent wasted time and effort in providers attempting to select patients from the virtual waiting room while the patients are unavailable (due to the patients working with the scheduling system).

If the scheduling system can schedule the remote encounter, then the scheduling system removes the patient from the virtual waiting room. For example, the list, table, or other data structure in a database that represents the patients waiting in the virtual waiting room is updated by removing the scheduled patient from the data structure, by removing a key associated with the patient in the data structure, or the like, so that the patient no longer occupies a spot in the queue for a remote encounter and can no longer be selected by a provider (until the patient re-enters the virtual waiting room for another remote encounter).

But if the scheduling system is not able to schedule the remote encounter, then the scheduling system returns the patient to the virtual waiting room without the patient losing his or her place in line. For example, data associated with the patient (for which the scheduling system could not find a mutually agreeable date and/or time for a scheduled remote encounter) can be changed to return the patient to the queue and allow the patient to be selected by a provider. This data can be changed by removing a lock key associated with the patient in a database (e.g., the REDIS memory structure) that prevents the patient from being selected by a provider, but without the patient losing his or her place in line. For example, if "Patient X" entered the waiting room on Monday, 17 May 2021, at 9:00 p.m.; waited until 9:30 p.m. before the scheduling system contacted Patient X to schedule a remote encounter; Patient X was made unavailable for selection by a provider while corresponding with the scheduling system; and was unable to schedule the remote encounter, then Patient X can go back into the queue but at the order that Patient X previously had. Patients still in the waiting room that entered the waiting room before Monday, 17 May 2021, at 9:00 p.m. would be ahead of Patient X in the order of the virtual waiting room, while patients that entered the virtual waiting room after Monday, 17 May 2021, at 9:00 p.m. would be behind Patient X, regardless of how long these patients have been in the virtual waiting room. This can reduce wait times for patients, as patients who are unable to schedule the encounter do not fall to the last or bottom of the queue.

The providers described herein may be healthcare providers while the consumers are patients in an embodiment for ease of illustration and explanation, although not all embodiments of the inventive subject matter are limited to healthcare services.

Figure 1:
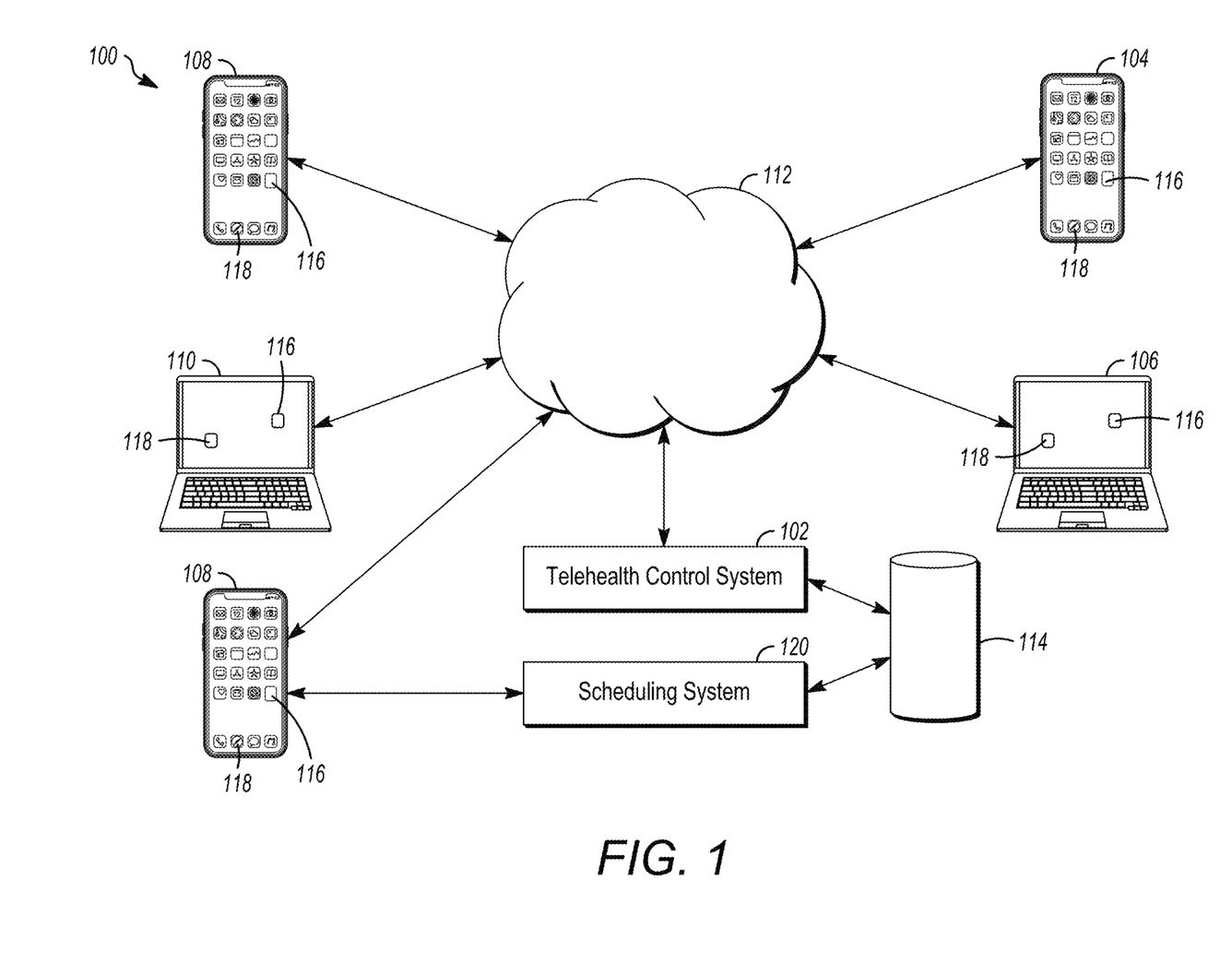
FIG. 1 illustrates one example of a telehealth system.

FIG. 1 illustrates one example of a telehealth system 100. The telehealth system 100 may be used to establish and conduct remote encounters between healthcare providers and patients. A remote encounter may include an interaction (e.g., meeting, medical appointment, medical consultation, etc.) between a healthcare provider and a patient via video conference or teleconference while the healthcare provider and the patient are in different locations (e.g., different rooms, different buildings, different towns or cities, different zip codes, different states, or different countries). The healthcare provider can be a Doctor of Medicine, Doctor of Osteopathy, a podiatrist, a dentist, a chiropractor, a clinical psychologist, an optometrist, a nurse practitioner, a nurse-midwife, or a clinical social worker. While the examples described herein relate to the system 100 being used to establish remote encounters between healthcare providers and patients, not all embodiments of the inventive subject matter are limited to telehealth systems. For example, the system 100 optionally can be used to establish and conduct remote encounters between real estate agents and clients, between attorneys and clients, courts and parties to a civil lawsuit or criminal court action, teachers and students, governmental meetings, voter and election systems, or any other service provider and customer who are connected via an electronic communication system.

The system 100 includes a telehealth control system 102 that represents hardware circuitry having and/or connected with one or more processors (e.g., microprocessors, field programmable gate arrays, integrated circuits, etc.) that perform the operations described in connection with the control system 102. The control system 102 communicates (wirelessly and/or via wired connections) with provider computing devices 104, 106 and consumer or patient computing devices 108, 110. The computing devices 104, 108 can represent laptop computers, desktop computers, tablet computers, or the like, and the computing devices 106, 110 can represent mobile phones.

The control system 102 can manage a virtual encounter between the providers and patients by establishing communication channels between a computing device 104 or 106 of the provider(s) and a computing device 108 or 110 of the patient. This communication channel can be a videoconference or a teleconference that extends through one or more computer networks 112, such as the Internet, one or more intranets, one or more local area networks, or the like. The computing devices 104, 106, 108, 110 may have software applications 116 installed or otherwise running thereon to establish a secure connection between (a) the provider computing device 104 or 106 and (b) the patient computing device 108 or 110. These software applications 116 can be commercial or proprietary applications 116 used by a company or government to manage the remote encounters between providers and patients. The applications 116 can be installed in internal computer memories of the computing devices 104, 106, 108, 110 or may be accessed via web pages 118. One example of such a software application 116 or service is MDLIVE healthcare services that provides remote healthcare services e.g., via telephone, video, email, mobile devices or a global computer network.

The secure connection can extend through the network(s) 112 and be encrypted or otherwise protected from outside parties to ensure confidentiality of the information communicated between the provider and the patient. For example, the videoconference or teleconference channel can extend through one or more digital subscriber lines, cable modems, network fibers, wireless networks, satellite networks, broadband over powerline connections, etc., using the transmission control protocol over Internet protocol, or another protocol.

A patient can submit a request for a virtual encounter to the control system 102 using the software application 116 installed on or accessible on a website 118 via a patient computing device 108 or 110. In FIG. 1, reference number 118 can represent this website that is accessed by an Internet browser. This request can identify the patient, one or more health consultation needs of the patient, and other information. The health consultation needs may identify health issues or questions that the patient wishes to have resolved, answered, or otherwise addressed by a remote encounter with a provider. The control system 102 can use this information to identify one or more appropriate providers. For example, if the request identifies an issue related to the skin of the patient, then the control system 102 can determine that the appropriate provider is a dermatologist. if the request identifies an issue related to diabetes mellitus, then the control system 102 can determine that the appropriate provider is an endocrinologist, and so on. The control system 102 may only send notifications to providers for the virtual encounters where the providers have education, expertise, training, and/or certification to provide service to treat the identified issue.

The control system 102 can include or have access to a tangible and non-transitory computer readable medium, such as a database within a computer memory 114, which stores different specialties of the providers, contact information (e.g., phone numbers) of the providers, and so on. The control system 102 can refer to information stored in the memory 114 to determine appropriate providers with which the videoconference or teleconference with the patient can be provided (based on information included in the request submitted by the patient).

Several patients may seek virtual appointments with the same type of physician (e.g., physicians with the same medical specialty) at the same time. The control system 102 may place these patients in a queue, or virtual waiting room. Providers can then send a message to the control system 102 (using the provider computing devices 104, 106) to accept a patient for a virtual encounter, e.g., through a first communication channel or through a secondary communication channel. The control system 102 can then establish a connection between the provider computing device 104 or 106 and the patient computing device 108 or 110 via the network(s) 112, such as a teleconference or videoconference, for the remote encounter to occur. The patient that is accepted for the virtual encounter is removed from the virtual waiting room. Other patients that continue to wait for selection for the virtual encounter can remain in the virtual waiting room.

Figure 2:
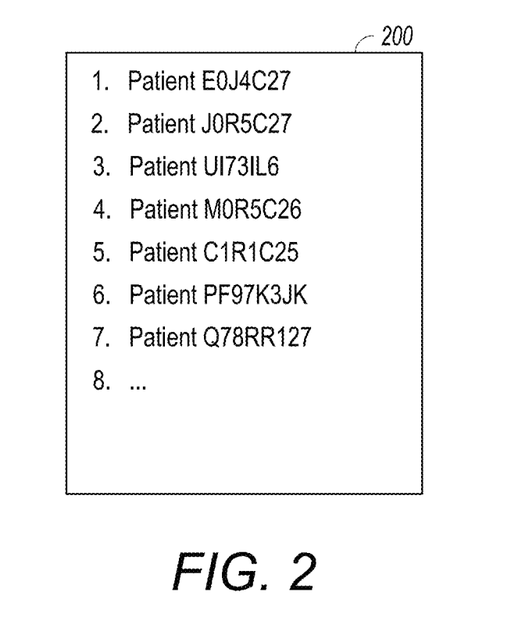
FIG. 2 illustrates an example of a virtual waiting room or queue.
Figure 3:
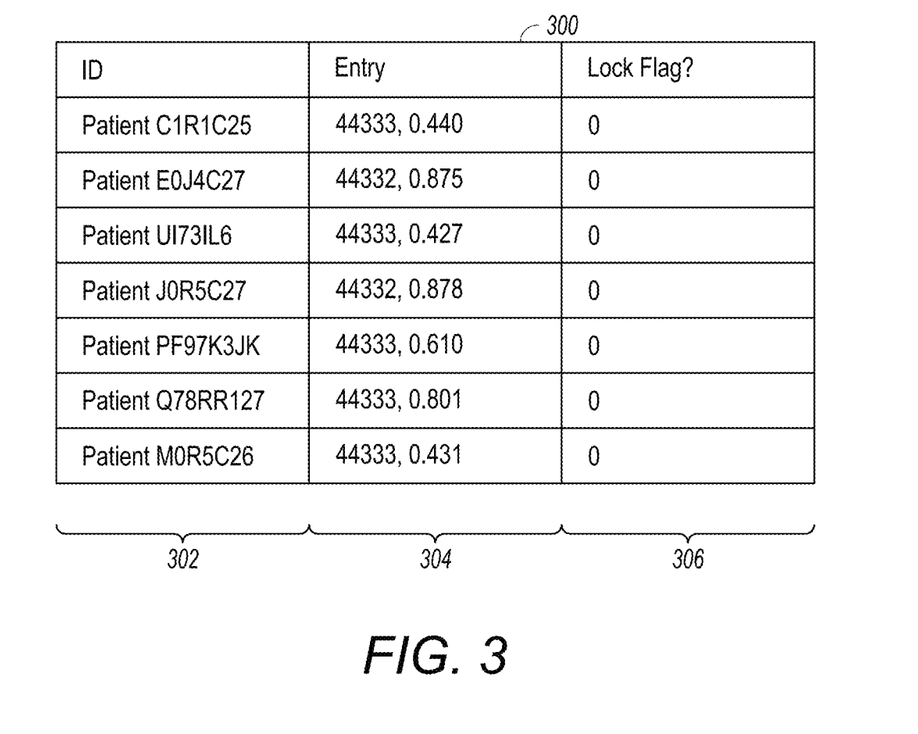
FIG. 3 illustrates an example of a data structure stored in a memory of the telehealth system shown in FIG. 1 in a state associated with the virtual waiting room or queue shown in FIG. 2.
Figure 4:
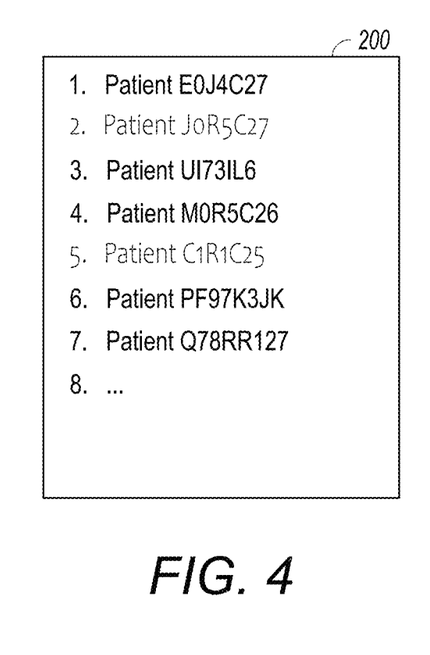
FIG. 4 illustrates another example of the virtual waiting room or queue.
Figure 5:
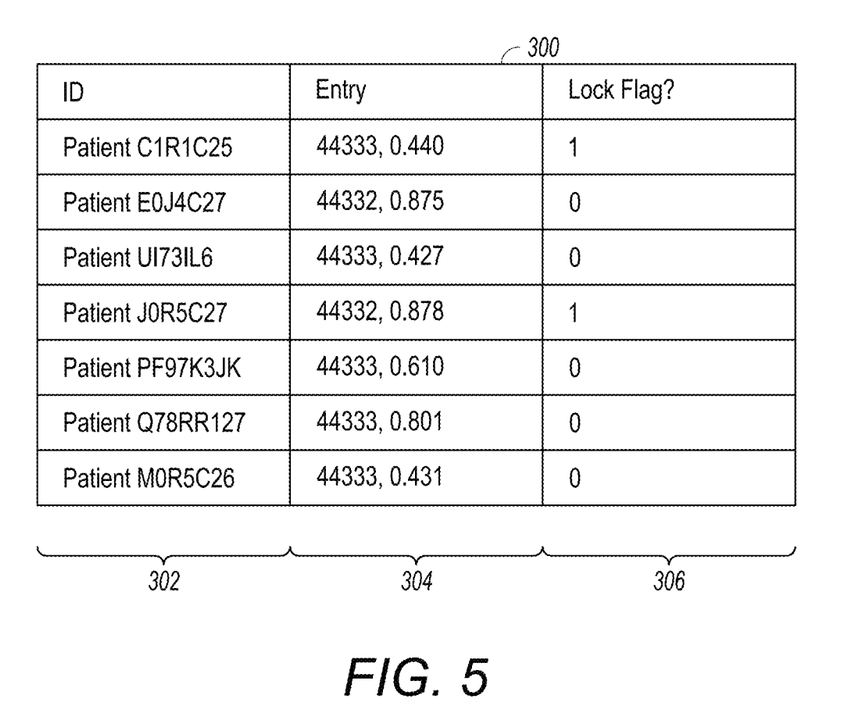
FIG. 5 illustrates another example of the data structure in a state associated with the virtual waiting room or queue shown in FIG. 4.
Figure 6:
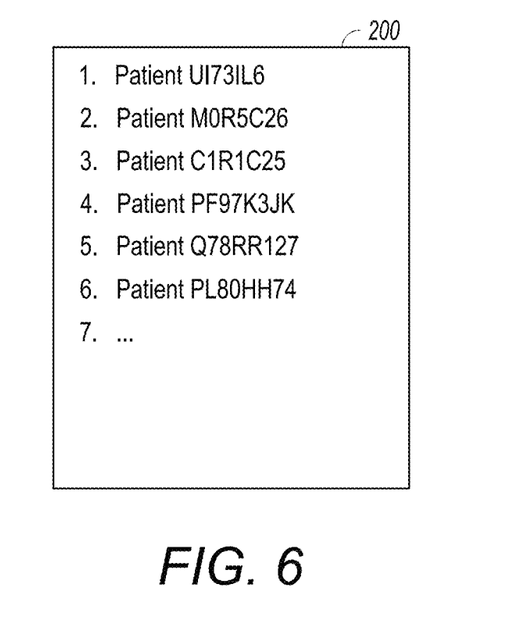
FIG. 6 illustrates another example of the virtual waiting room or queue.
Figure 7:
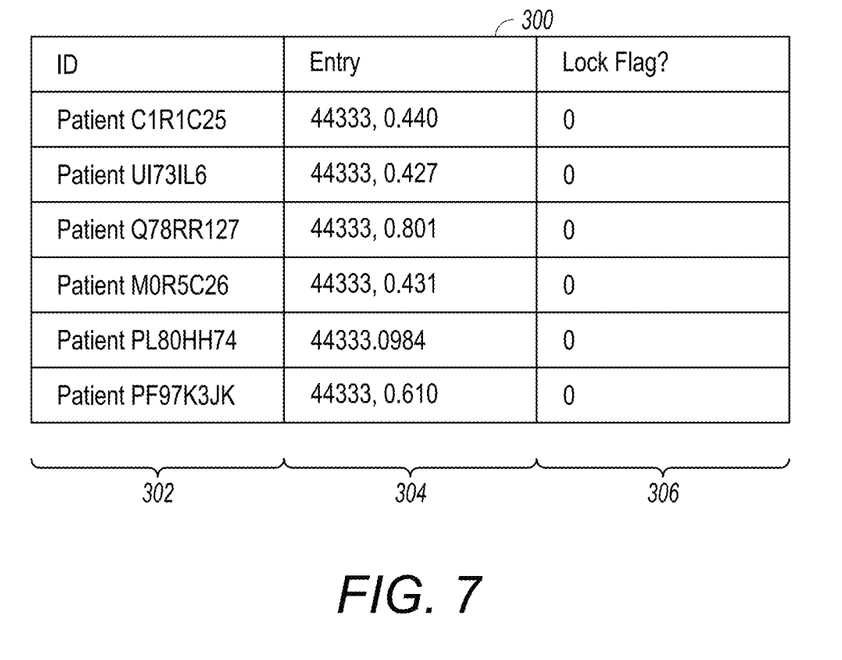
FIG. 7 illustrates another example of the data structure in a state associated with the virtual waiting room or queue shown in FIG. 6.

With continued reference to the control system 102 shown in FIG. 1, FIGS. 2, 4, and 6 illustrate examples of a virtual waiting room or queue 200 and FIGS. 3, 5, and 7 illustrate examples of a data structure 300 stored in the memory 114 shown in FIG. 1. The data structure 300 shown in FIG. 3 is associated with the virtual waiting room or queue 200 shown in FIG. 2, the data structure 300 shown in FIG. 5 is associated with the virtual waiting room or queue 200 shown in FIG. 4, and so on.

The virtual waiting room or queue 200 can represent a GUI that the control system 102 directs the application 116 or website 118 to display to the providers to notify the providers of the patients that are waiting for a virtual encounter. The virtual waiting room or queue 200 can list the patients in order that the patients entered the virtual waiting room or queue 200. For example, the control system 102 can store, in the data structure 300 in the memory 114 (e.g., a list, table, or the like), entries 302 that indicate the date and/or time that each patient (identified by unique identifiers 304) that is still in the waiting room 200 requested a virtual encounter or were otherwise placed in line to wait for the next available applicable provider (e.g., based on patient input). The control system 102 can refer to the data structure 300 to determine the order in line that each patient has in the virtual waiting room or queue 200. In the illustrated example, patient E0J4C27 entered the virtual waiting room or queue 200 before the other patients J0R5C27, UI73IL6, M0R5C26, C1R1C25, PF97K3JK, Q78RR127, and so on, and remains in the virtual waiting room or queue 200. Therefore, patient E0J4C27 is at the front of the line in the queue 200. Patient J0R5C27 entered after patient E0J4C27, but before the other patients, so patient J0R5C27 is next in line, and so on.

The telehealth system 100 can include a scheduling system 120 that represents hardware circuitry that includes and/or is connected with one or more processors that perform the operations described in connection with the scheduling system 120. The scheduling system 120 can repeatedly check the data structure 300 to determine how long different patients have been waiting for a virtual encounter in the queue or virtual waiting room 200. If this waiting time for any patient meets or exceeds a threshold time period, then the scheduling system 120 can automatically contact the patient to try and schedule an upcoming date and/or time for the virtual encounter. For example, the scheduling system 120 can automatically call, text, email, or otherwise contact the patient computing device 108, 110 to try and find a time and date that the patient and a provider are available for a virtual encounter. If such a time and date are found, then the virtual encounter can be scheduled for that time (by adding data to the data structure 300 to schedule the virtual encounter) and the patient removed from the virtual waiting room or queue 200. The patient can then attend the virtual encounter with the provider via the telehealth system 100 at the scheduled date and time.

One or more patients may be added to or removed from the virtual waiting room or queue 200 while a patient is speaking or corresponding with the scheduling system 120 to try and schedule an upcoming virtual encounter. For example, Patient J0R5C27 and Patient C1R1C25 may be separately contacted by the scheduling system 120 to try and schedule upcoming dates and/or times for virtual encounters for each of these patients. Because these patients may be preoccupied with speaking or corresponding with the scheduling system 120 to schedule encounters, the patients may not be available or attentive for a virtual encounter. As a result, the scheduling system 120 can effectively hold these patients out of the queue 200 until a date and time for the encounter is scheduled or the conversation or correspondence between the scheduling system 120 and the patient is terminated. During the time period that the patients are held out of the queue 200, other patients in the queue can continue to be selected for virtual encounters as providers become available. But the patients that are speaking or corresponding with the scheduling system 120 may be held out and not available for selection by providers.

FIG. 4 illustrates an updated version of the virtual waiting room or queue 300 shown in FIG. 3 with Patients J0R5C27 and C1R1C25 being held out from selection by providers for virtual encounters. The scheduling system 120 can add or change the value of data in the data structure 300 to indicate that the scheduling system 120 is actively speaking or corresponding with Patients J0R5C27 and C1R1C25. For example, the data structure 300 can include lock flags 306 having values that indicate whether the patient is available for selection and entry into a virtual encounter with a provider, or that the patient is not available for selection and entry into the virtual encounter with a provider. The presence of the lock flag 306 or the value of the lock flag 306 associated with a patient identifier 302 in the data structure 300 indicates that the patient remains in the queue or virtual waiting room 200 but is unavailable for selection by a provider. Based on the presence or value of the lock flag 306, the control system 102 can change how the patient appears in the queue or virtual waiting room 200 or can remove the patient from the list in the virtual waiting room 200 (but without the patient losing his or her place in line).

For example, in FIG. 3, the value of the lock flags 306 for the patients in the virtual waiting room or queue 200 is zero (or no lock flags 306 are present) in the data structure 300. This indicates that none of these patients currently is occupied with the scheduling system 120. As a result, each of the patients listed in FIGS. 2 and 3 currently is available for selection by a provider (and is therefore shown in the virtual waiting room or queue 200). But when Patients J0R5C27 and C1R1C25 are contacted by the scheduling system 120 to try and schedule virtual encounters, the scheduling system 120 can insert the lock flag 306 or change the value of the lock flag 306 in the data structure 300 to indicate that Patients J0R5C27 and C1R1C25 are not currently available for selection by a provider in the virtual waiting room or queue 200. As a result, the lock flags 306 are present or the values of the lock flags 306 in the data structure 300 are changed (e.g., from 0 to 1) to indicate that Patients J0R5C27 and C1R1C25 are not currently available for selection by a provider for a virtual encounter, as shown in FIG. 5.

The control system 102 can change the appearance of the patient in the virtual waiting room or queue 200 responsive to the lock flag 306 being added to the data structure 300 or the value of the lock flag 306 being changed. For example, the control system 102 can make the patient identifier less clear (e.g., in different color font, such as a gray color, as shown in FIG. 4) or can no longer list the patient identifier in the virtual waiting room or queue 200. This can inform providers and/or prevent providers from selecting the patients (that are working with the scheduling system 120 to schedule the encounter) for a virtual encounter. Instead, the providers can select the next patient for the virtual encounter (e.g., Patients E0J4C27, UI73IL6, M0R5C26, PF97K3JK, Q78RR127, and the like). Stated differently, the patients that are working (e.g., speaking or corresponding) with the scheduling system 120 are locked out or otherwise prevented from being selected by a provider to initiate the virtual encounter. Instead, the providers can select other patients in the virtual waiting room or queue 200 (e.g., the next patient in line or the first patient in line).

But not all patients may be able to find an available date or time to schedule a virtual encounter via the scheduling system 120 and/or some patients may prefer to continue waiting in the virtual waiting room or queue 200 for the next available provider. The scheduling system 120 can place patients that are unable or unwilling to schedule the encounter via the scheduling system 120 back into the virtual waiting room or queue 200. The scheduling system 120 can place these patients back into the virtual waiting room or queue 200 without the patients losing their place in line. For example, the scheduling system 120 can change the data structure 300 by removing the lock flag 306 or changing the value of the lock flag 306 (e.g., from 1 to 0, as shown in FIG. 7) for the patient identifiers 302 of patients that return to the virtual waiting room or queue 200.

Responsive to the data structure 300 being updated to reflect that a patient is no longer working with the scheduling system 120, the control system 102 can update the virtual waiting room or queue 200 that is presented to the providers on the provider computing devices 104, 106. As shown in FIG. 6, the virtual waiting room or queue 200 is updated to show that Patient C1R1C25 is back in the virtual waiting room or queue 200. Patient J0R5C27 has been removed from the virtual waiting room or queue 200 as this patient was able to schedule an upcoming virtual encounter via the scheduling system 102. The scheduling system 102 can remove or otherwise change the data associated with the identifier 302 for Patient J0R5C27 to indicate that the patient is no longer to be included or displayed on the provider computing devices 104, 106 as waiting in the virtual waiting room or queue 200.

The patients that are unable to schedule the appointment and that are returned to the virtual waiting room or queue 200, however, do not lose their place in line. The scheduling system 120 can remove the lock flag 306 or change the value of the lock flag 306 in the data structure 300 for those patients that return to the virtual waiting room or queue 200. The control system 102 displays the waiting room or queue 200 (or directs the provider computing devices 104, 106 to display via the application 116 or website 118) with these patients returned to their place in line. For example, the patients that were unable to schedule the encounter with the scheduling system 120 (e.g., "unscheduled patients") can be returned to the virtual waiting room or queue 200 in a position or order that is behind other patients that entered the virtual waiting room or queue 200 before the unscheduled patient(s) but ahead of other patients that entered the virtual waiting room or queue 200, regardless of whether any of these patients were temporarily unavailable for selection by providers in the virtual waiting room or queue 200 (due to correspondence with the scheduling system 120).

In the example of FIGS. 2 through 7, Patients J0R5C27 and C1R1C25 were temporarily unavailable in the virtual waiting room or queue 200 for selection by a provider while Patients J0R5C27 and C1R1C25 were conversing with the scheduling system 120 (as shown in FIG. 4). Patient J0R5C27 was able to schedule an upcoming appointment with a provider, so was removed from the virtual waiting room or queue 200 (as shown in FIG. 6 and removal of this patient from the data structure 300 shown in FIG. 7). Patient C1R1C25 was not able to schedule an appointment, so this patient was returned to the virtual waiting room or queue 200 (as shown in FIG. 6 and the changed value of the lock flag 306 in the data structure 300 shown in FIG. 7). Patient E0J4C27 was selected by a provider for an encounter and Patient J0R5C27 was able to schedule an encounter, so both these patients were removed from the virtual waiting room or queue 200 (as shown in FIGS. 6 and 7). Patient C1R1C25 did not lose his or her place in line behind the patients already ahead of Patient C1R1C25 (e.g., Patients UI73IL6 and M0R5C26). The data structure 300 maintained the entry time and date 304 of Patient C1R1C25, so that patient did not lose the place in line behind Patients UI73IL6 and M0R5C26 and remains ahead of Patients PF97K3JK and Q78RR127. Additionally, new patients that enter the virtual waiting room or queue 200 while another patient is working with the scheduling system 120 remain behind the patient working with the scheduling system 120. That is, a new patient (e.g., Patient PL80HH74) that enters the virtual waiting room or queue 200 while Patient C1R1C25 was corresponding with the scheduling system 120 remains behind Patient C1R1C25 when Patient C1R1C25 returns to the virtual waiting room or queue 200 after being unable to schedule the encounter.

Figure 10:
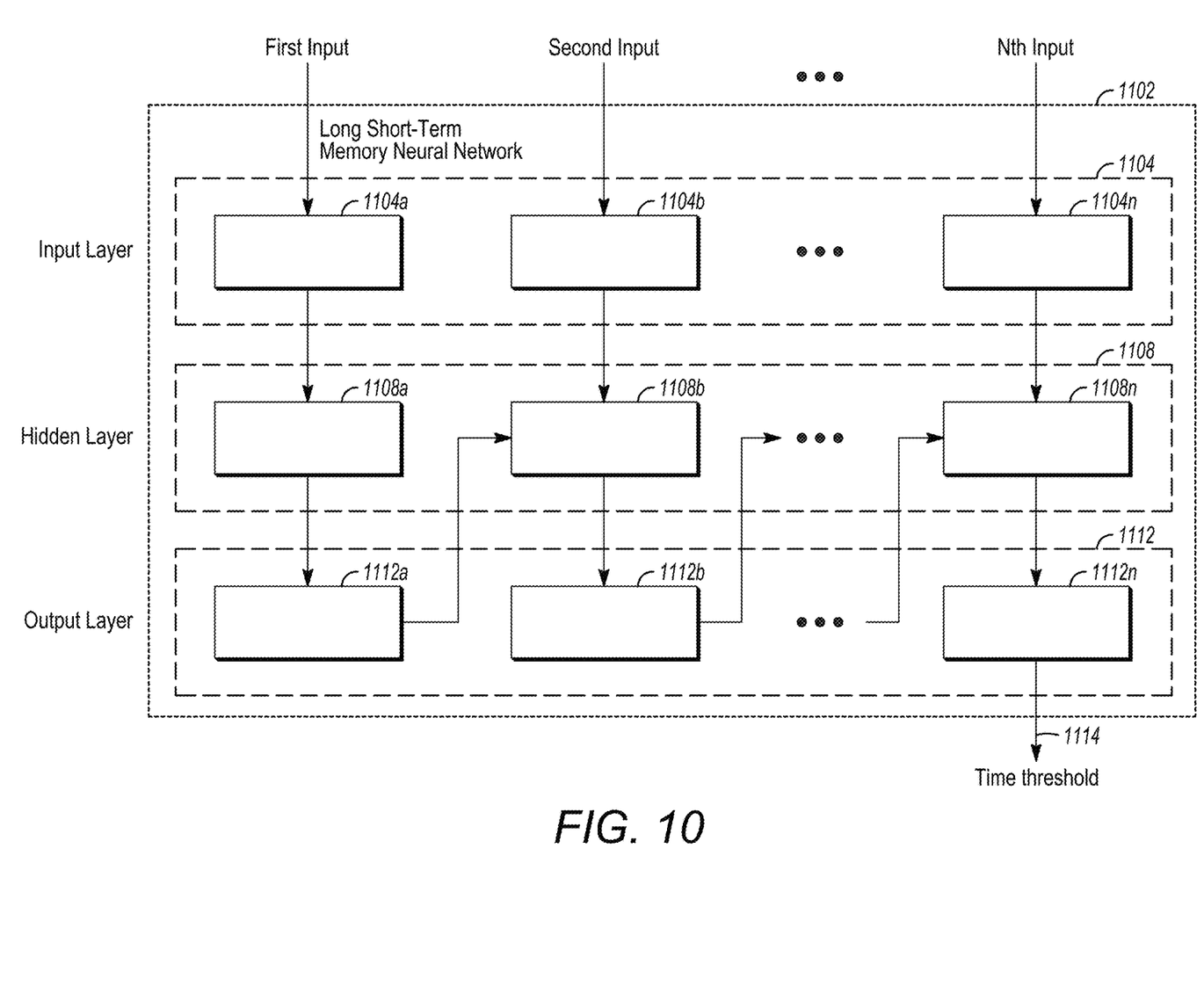
FIG. 10 is a functional block diagram of an example neural network that can be used for the prediction engine or other functions (e.g., engines).

In an example embodiment, the present systems and methods can provide a time threshold on the lock flag. The timing threshold can be set to a maximum time that the patient device and the system can set an appointment record that agrees with the patient availability and a provider availability. The provider availability can be a set record in the system or can inquire a provider device whether the provider can accept the appointment as proposed. If the time it takes to set an appointment record exceeds the timing threshold the system will remove the lock flag from the record 300. This will return the patient to the virtual waiting room queue 200. The patient record may remain in the queue 200 as described herein and be reactivated for connection to a provider device when the lock flag is removed. The timing threshold can be a dynamic setting based on prior scheduling history based on patient data and provider data. The present systems and methods can use machine learning or artificial intelligence to set the timing threshold. FIG. 10 and related description throughout the present application describes the dynamic nature of setting the timing threshold in greater detail.

In an example embodiment, the present systems 100 and methods can provide a visit type value, which can be stored in the patient record, e.g., in database within computer memory 114. The visit type value can be based on the information provided related to the virtual visit, e.g., from the patient device 108 or 110. The visit type value can prevent a patient from being locked out of the patient queue. For example, certain identified visits are not eligible for asynchronous visits with a provider. These visits have a visit value that does not allow the patient to be locked out of the queue. The visit type value can control whether or not the lock out flag can be set to a lock out value and whether the patient always stays active in the queue.

Figure 8:
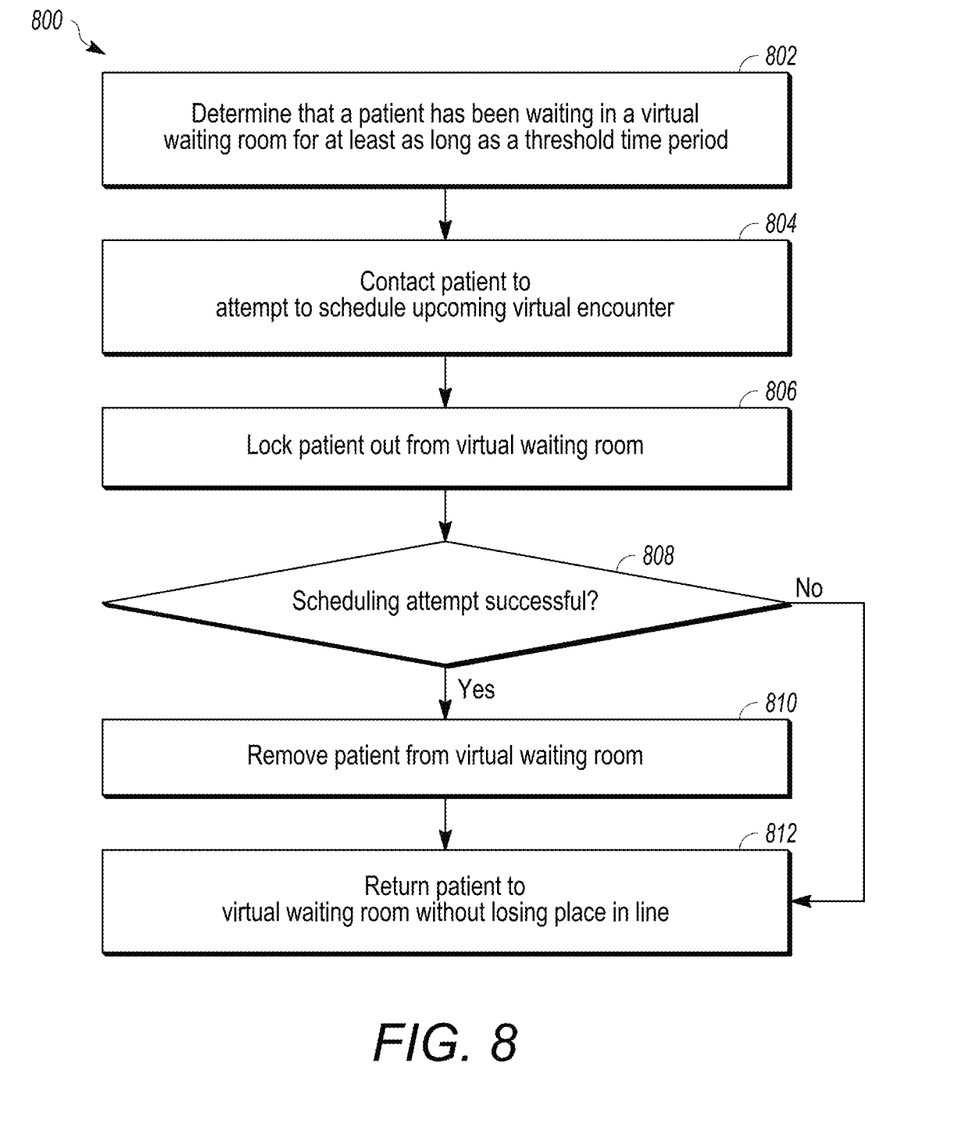
FIG. 8 illustrates a flowchart of one example of a method for managing a virtual waiting room or queue for a telehealth system.

FIG. 8 illustrates a flowchart of one example of a method 800 for managing a virtual waiting room or queue for a telehealth system. The method 800 can represent operations performed by the control system 102 and/or scheduling system 120 shown in FIG. 1. At 802, a determination is made that one or more patients have been waiting for a virtual encounter in a virtual waiting room or queue for at least as long as a threshold time period. For example, the scheduling system 120 can compare the time entries 304 for the patients with a current time and/or date to determine how long each patient has been in the virtual waiting room or queue 200. At 804, the patient that has been waiting at least as long as the threshold time period is contacted to try and schedule the upcoming virtual encounter. For example, instead of the patient continuing to wait in the virtual waiting room, the scheduling system 120 can call or initiate a call between the patient and the scheduling system 120 (or a person operating the scheduling system 120).

At 806, the patient is locked out (for selection) from the virtual waiting room. The scheduling system 120 can change the value of a lock flag 306, add data to the data structure 300, or otherwise indicate that the patient cannot be selected from the virtual waiting room 200 by a provider computing device 104, 106 for a virtual encounter. The patient's name or identifier may be removed from the virtual waiting room 200 (without the patient losing his or her place in line) or the appearance of the patient's name or identifier may change to indicate that the patient is currently locked out from being selected by a provider for a virtual encounter. An attempt by a provider computing device 104, 106 to select a locked-out patient from the virtual waiting room 200 may be ignored, disregarded, or rejected by the control system 102.

At 808, a decision is made as to whether the patient was able to schedule an upcoming virtual encounter with the scheduling system 120. If the patient was able to schedule such an appointment, the patient may no longer need to return to the virtual waiting room 200. As a result, flow of the method 800 can proceed toward 810. But if the patient was not able to schedule the appointment, the patient may return to the virtual waiting room 200 to wait for a provider to select the patient. As a result, flow of the method 800 can proceed toward 812.

At 810, the patient is removed from the virtual waiting room 200. For example, the scheduling system 120 may remove the patient identifier 302 from the data structure 300 or otherwise change the data structure 300 to indicate that the patient is no longer to be listed in the virtual waiting room 200 (for selection by a provider). Flow of the method 800 can terminate or return to one or more prior operations (e.g., 802).

At 812, the patient is returned to the virtual waiting room 200 without losing his or her place in line. The scheduling system 120 can change the data structure 300 (e.g., by removing or changing the lock flag 306 of that patient) to indicate that the patient has returned to waiting for selection by a provider for a virtual encounter. This can prevent the patient from losing his or her place in line, as described above. Flow of the method 800 can terminate or return to one or more prior operations (e.g., 802).

Figure 9:
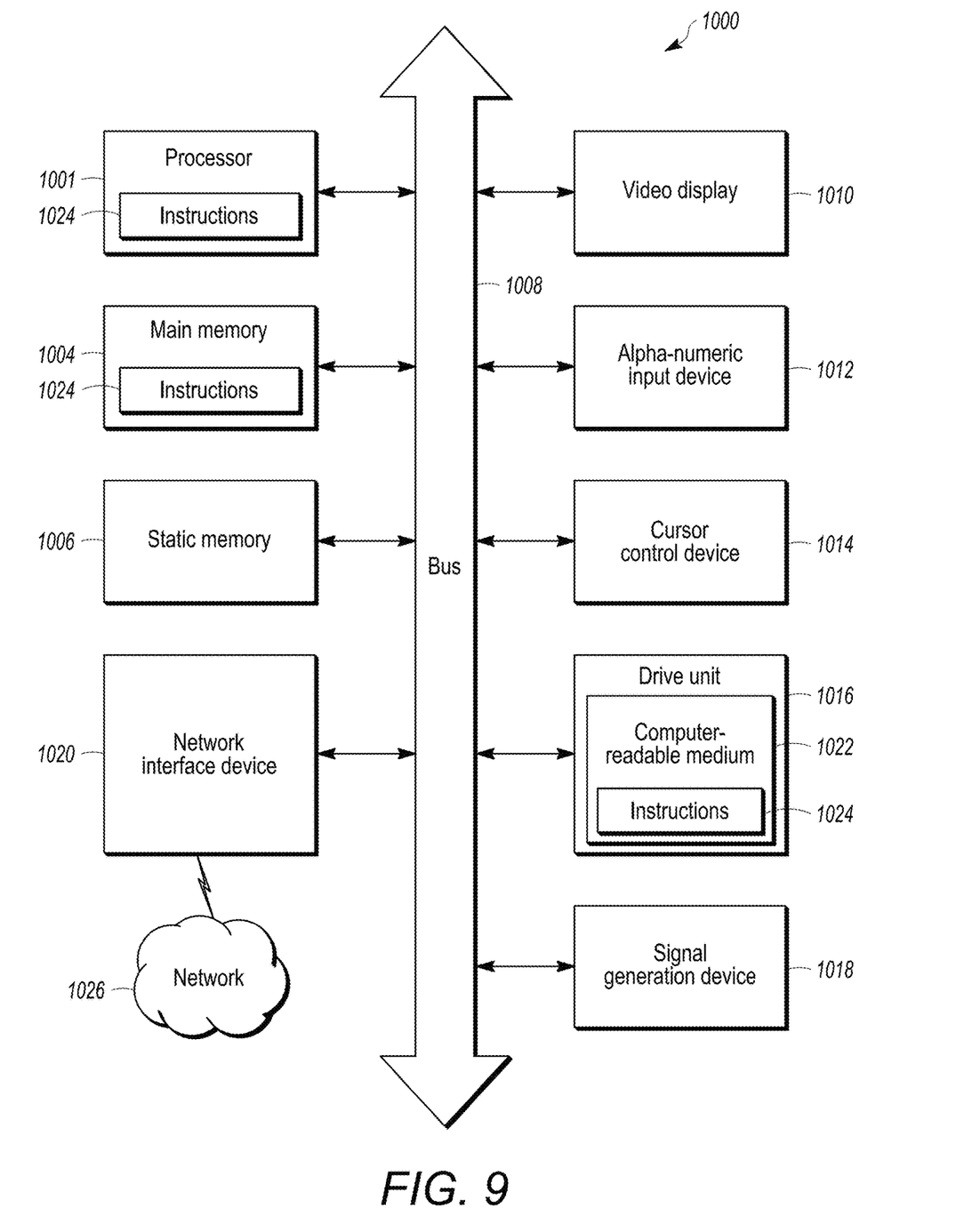
FIG. 9 shows a block diagram of a computer system within which a set of instructions may be executed causing the machine to perform any one or more than one methods, processes, operations, or methodologies discussed herein.

FIG. 9 shows a block diagram of a computer system 1000 within which a set of instructions may be executed causing the machine to perform any one or more than one methods, processes, operations, or methodologies discussed herein. For example, the system 1000 may represent the control system 102 and/or scheduling system 120 shown in FIG. 1. The devices 1006-1030, for example, may include the functionality of the computer system 1000. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1000 includes a processor 1002 (e.g., a central processing unit (CPU), a graphics processing unit (GPU) or both, etc.), a main memory 1004 and a static memory 1006, which communicate with each other via a bus 1008. The computer system 1000 further includes a video display unit 1010 (e.g., a liquid crystal display (LCD) or a cathode ray tube (CRT), etc.). The computer system 1000 also includes an alphanumeric input device 1012 (e.g., a keyboard, etc.), a cursor control device 1014 (e.g., a mouse, etc.), a drive unit 1016, a signal generation device 1018 (e.g., a speaker, etc.) and a network interface device 1020.

The drive unit 1016 includes a computer readable medium 1022 on which is stored one or more than one sets of instructions 1024 (e.g., software, etc.) embodying any one or more than one methodologies or functions described herein. The instructions 1024 may also reside, completely or at least partially, within the main memory 1004 and/or within the processor 1002 during execution thereof by the computer system 1000, the main memory 1004 and the processor 1002 also constituting non-transitory computer readable media. When loaded with the instructions 1024, the processor 1002 is a machine dedicated to only the present processes and methodologies.

The instructions 1024 may further be transmitted or received over a network 1026 via the network interface device 1020. The instructions can implement multiple communication channels to a provider, e.g., to multiple provider devices and the telehealth control system with one channel being a patient channel that provides data related to the patient and providing connection directly to the patient and a second channel that is a packet channel to provide text messages (e.g., non-video or non-audio communication). The network 1026 can represent the network(s) 112 shown in FIG. 1. While the computer-readable medium 1022 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The present disclosure uses the term message for describing communication over a secondary communication channel to and from the provider devices. In an example embodiment, the message is not an audio signal. In an example embodiment, the message is not a video signal. Messages can be SMS text messages in an example embodiment. The messages can be packets including a header (including sender device and recipient device identification data) and a body of data. The use of a packet for communication on the second channel can allow for the packet to require less bandwidth to route the information to and from the provider device. Routing the packets can use internet protocol (e.g., IPv4, IPv6 and the like) to transmit the packets. The packet replies from the provider device can be a selection reply, e.g., a single character, that in and of itself does not provide any protected or sensitive information and can be interpreted by the telehealth system.

FIG. 10 is a functional block diagram of an example neural network 1102 that can be used for the prediction engine or other functions (e.g., engines) as described herein. In an example, the prediction engine can dynamically determine the timing threshold for the lock flag (e.g., how long the designated wait time period is that a patient waits in a queue before the scheduling system of the telehealth system automatically reaches out to the patient to schedule a date and/or time for a virtual encounter). In an example, the neural network 1102 can be a LSTM neural network. In an example, the neural network 1102 can be a recurrent neural networks (RNN). The example neural network 1102 may be used to implement the machine learning as described herein, and various implementations may use other types of machine learning networks. The neural network 1102 includes an input layer 1104, a hidden layer 1108, and an output layer 1112. The input layer 1104 includes inputs 1104a, 1104b . . . 1104n. The hidden layer 1108 includes neurons 1108a, 1108b . . . 1108n. The output layer 1112 includes outputs 1112a, 1112b . . . 1112n.

Each neuron of the hidden layer 1108 receives an input from the input layer 1104 and outputs a value to the corresponding output in the output layer 1112. For example, the neuron 1108a receives an input from the input 1104a and outputs a value to the output 1112a. Each neuron, other than the neuron 1108a, also receives an output of a previous neuron as an input. For example, the neuron 1108b receives inputs from the input 1104*b* and the output 1112*a*. In this way the output of each neuron is fed forward to the next neuron in the hidden layer 1108. The last output 1112*n* in the output layer 1112 outputs a probability associated with the inputs 1104*a*-1104*n*. Although the input layer 1104, the hidden layer 1108, and the output layer 1112 are depicted as each including three elements, each layer may contain any number of elements. In various implementations, each layer of the neural network 1102 may include the same number of elements as each of the other layers of the neural network 1102. Alternatively, the layers may have different numbers of elements.

The outputs determined by the various neurons may be calculated using one or more models, such as one or more groups of equations, that are used to calculate the output based on the corresponding input. For example, historical patient data (e.g., patient scheduling data) may be processed to create the inputs 1104*a*-1104*n*. In an example, historical provider data (e.g., provider scheduling data) may be processed to create the inputs 1104*a*-1104*n*. The output of the neural network 1102 may represent a time threshold or a time threshold range. More specifically, the inputs 1104*a*-1104*n* can include known scheduling timing data stored in the storage device 114. Such timing data can be provided to neurons 1108*a*-1108*n* for analysis and connections between various factors involved in time to set an appointment. The inputs 1104*a*-1104*n* may include timing data related to system available data (e.g., date based timing, number of providers available, number of providers available based on geographic location, issue for which a patient is seeking to see a provider, a prediction of wait time in the virtual waiting room, and the like). The neurons 1108*a*-1108*n*, upon finding connections provides the potential connections as outputs to the output layer 1112, which determines a timing threshold, e.g., a value or a range. The output layer 1112 can confirm dynamically adjusted timing threshold and provide same to the system to determine whether it should adjust the timing threshold. The system can have limits on adjusting the timing threshold (e.g., the threshold is not adjusted unless the change is greater than five percent of the prior value). Such a limit on changing the timing threshold value in the present system or process can be built into the neural network 1102 (e.g., be an input 1104*b*-1104*n*).

The output from the output layer 1112 can be examined to determine feedback data. The feedback data can indicate whether the timing threshold (as adjusted or as remaining the same based on this output) is acceptable or not. For example, if the timing threshold results in fewer or less than a threshold number, fraction, or percentage of the patients scheduling their telehealth appointments instead of waiting in the queue, then the feedback data can indicate that the timing threshold is not acceptable. Conversely, if the timing threshold results in at least the threshold number, fraction, or percentage of the patients scheduling their telehealth appointments instead of waiting in the queue, then the feedback data can indicate that the timing threshold is acceptable. The feedback data can be provided as input back to the neural network and one or more of the models (used by the neurons to calculate the respective outputs of the neurons) can be modified based on the feedback data. For example, one or more of the models can be changed such that the same input provided to the model(s) as before results in a different output. This can result in a different timing threshold being output by the neural network even if the same input(s) as before are provided. In this way, the neural network can repeatedly update or change the models and improve operation in selection of different timing thresholds over time.

In some embodiments, a convolutional neural network may be implemented. Similar to neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 1104*a* is connected to each of neurons 1108*a*, 1108*b* . . . 1108*n*.

In various implementations, each input node in the input layer may be associated with a numerical value, which can be any real number. In each layer, each connection that departs from an input node has a weight associated with it, which can also be any real number. In the input layer, the number of neurons equals number of features (columns) in a dataset. The output layer may have multiple continuous outputs.

As mentioned above, the layers between the input and output layers are hidden layers. The number of hidden layers can be one or more (one hidden layer may be sufficient for many applications). A neural network with no hidden layers can represent linear separable functions or decisions. A neural network with one hidden layer can perform continuous mapping from one finite space to another. A neural network with two hidden layers can approximate any smooth mapping to any accuracy.

Additional factors that can be used by the prediction engine (e.g., the neural network 1102), may include, but is not limited to, patient journey, patient history, and patient preferences. In an example, the system can inquire, through an interactive survey electronically sent to the patient device, whether the patient would prefer to schedule a visit with a provider rather than wait in the virtual waiting room.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information, but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims is intended to be a means-plus-function element within the meaning of 35 U.S.C. § 112(f) unless an element is expressly recited using the phrase "means for," or in the case of a method claim using the phrases "operation for" or "step for."

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

The use of the present methods and systems may operate to reduce conflicting resource usage (e.g., a scheduling process and a real-time connection process) executing on a same contact (e.g., a data structure dedicated to an individual patient) at the same time. A reduction in conflicting resources may provide an efficient use of healthcare resources (e.g., reduction in dropped communication connections, efficient connection of patient devices with provider devices through a medical network, and the like).

Some embodiments described herein provide a systematic way of connecting patients with providers in a remote healthcare setting (e.g., telehealth). The system can identify patients in a virtual waiting room that may best be served through less time in the virtual waiting room and scheduling a consultation connection with a provider through communication devices. For example, the patient can be identified using patient specific data and system data relating to consultations of other patients. A scheduling engine can set a lock flag on the patient record while the scheduling process occurs. The lock flag can have a time threshold. A further dynamic prediction engine can set the time threshold. Some of the embodiments herein relate to patient relationship management and, more particularly, to enhancing the patient experience by providing alternative virtual connection avenues relative to merely waiting in the virtual waiting room while maintaining a patient's rank in the waiting room queue. The embodiments herein enhance the patient experience by dynamically selecting patients to be locked in the queue while launching and conducting a future scheduling function in an online environment.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

What is claimed is:

1. A method comprising:
providing remote access of a telehealth system across a network to plural healthcare provider devices associated with plural healthcare providers to allow the plural healthcare providers to conduct a virtual encounter with patients;
directing applications of the plural healthcare provider devices each associated with the healthcare provider to notify the plural healthcare providers that one or more of the patients are available for the virtual encounter;
establishing a first wireless connection across the network between a first healthcare provider device of the plural healthcare provider devices and a first patient device of a first patient of the one or more of the patients responsive to receiving a request from the first healthcare provider device for the virtual encounter with the first patient;
examining a data structure stored in a database of a telehealth system to determine whether a second patient having a waiting location in an order among the patients in a virtual waiting room for the virtual encounter with the plural healthcare providers has been waiting at least as long as a threshold time period;
responsive to determining that the second patient has been waiting for at least as long as the threshold time period, changing the data structure stored in the database of the telehealth system to indicate that the second patient is locked out of the virtual waiting room while a scheduling system of the telehealth system attempts to schedule an upcoming virtual appointment involving the second patient, wherein changing the data structure changes a digital display of the applications of the plural healthcare provider devices to change an appearance of the second patient in the virtual waiting room displayed in the applications to indicate that the second patient is not available for the virtual encounter;
responsive to the scheduling system being unable to schedule the upcoming virtual appointment involving the second patient, changing the data structure stored in the database of the telehealth system to return the second patient to the virtual waiting room without the second patient losing the waiting location in the order of the virtual waiting room with a second patient device associated with the second patient indicated as an available communication connection with the healthcare provider devices in the database of the telehealth system, wherein changing the data structure to return the second patient to the virtual waiting room changes the digital display of the applications of the plural healthcare provider devices to change the appearance of the second patient in the virtual waiting room displayed in the applications to indicate that the second patient is available for the virtual encounter; and
establishing a second wireless connection across the network between the first healthcare provider device and the second patient device after changing the data structure to return the second patient to the virtual waiting room.

2. The method of claim 1, further comprising:
calculating the threshold time period using an artificial intelligence (AI) neural network and one or more models of the AI neural network;
using the threshold time period obtained from the AI neural network to determine whether the second patient has been waiting for at least as long as the threshold time period;
providing feedback to the AI neural network indicating that the second patient was unable to schedule the upcoming virtual appointment;
changing the one or more models of the AI neural network based on the feedback that is provided to the AI neural network; and changing the threshold time period using the AI neural network and based on the one or more models that are changed.

3. The method of claim 1, wherein the second patient cannot be selected by any of the plural healthcare providers for the virtual encounter while the second patient is locked out of the virtual waiting room.

4. The method of claim 1, wherein the data structure stored in the database of the telehealth system is changed to indicate the second patient is locked out of the virtual waiting room by adding a lock flag or changing a value of the lock flag in the data structure.

5. The method of claim 4, wherein the data structure stored in the database of the telehealth system is changed to return the second patient to the virtual waiting room without the second patient losing the waiting location in the order of the virtual waiting room by removing the lock flag or changing the value of the lock flag in the data structure.

6. The method of claim 1, wherein the data structure stored in the database of the telehealth system is changed to return the second patient to the virtual waiting room without the second patient losing the waiting location in the order of the virtual waiting room such that one or more prior patients that entered the virtual waiting room before the second patient are ahead of the second patient in the virtual waiting room and one or more subsequent patients that entered the virtual waiting room after the second patient are behind the second patient in the virtual waiting room.

7. The method of claim 6, wherein at least one of the one or more subsequent patients entered the virtual waiting room while the second patient was working with the scheduling system to schedule the upcoming virtual appointment.

8. The method of claim 1, further comprising:
changing the data structure stored in the database of the telehealth system to remove the second patient from the virtual waiting room responsive to the scheduling system successfully scheduling the upcoming virtual appointment involving the second patient.

9. A telehealth system comprising:
one or more processors of a scheduling system configured to direct applications of plural healthcare provider devices each associated with a healthcare provider to notify plural healthcare providers that patients are available for a virtual encounter, wherein the one or more processors are configured to provide remote access of a telehealth system across a network to each of the plural healthcare provider devices to allow the healthcare provider to conduct the virtual encounter with the patients,
the one or more processors configured to establish a first wireless connection across the network between a first healthcare provider device of the plural healthcare provider devices and a first patient device of a first patient of the patients responsive to receiving a request from one of the healthcare provider devices for the virtual encounter,
the one or more processors configured to examine a data structure stored in a database of the telehealth system to determine whether a second patient of the patients having a waiting location in an order among the patients in a virtual waiting room for the virtual encounter with one of the plural healthcare providers has been waiting at least as long as a threshold time period, the one or more processors configured to change the data structure stored in the database of the telehealth system responsive to determining that the second patient has been waiting for at least as long as the threshold time period,
the one or more processors configured to change the data structure to indicate that the second patient is locked out of the virtual waiting room while the scheduling system attempts to schedule an upcoming virtual appointment involving the second patient, wherein the one or more processors are configured to change the data structure to change a digital display of each of the applications of the plural health provider devices to change an appearance of the second patient in the virtual waiting room displayed in the applications to indicate that the second patient is not available for the virtual encounter,
the one or more processors configured to change the data structure stored in the database of the telehealth system to return the second patient to the virtual waiting room without the second patient losing the waiting location in the order of the virtual waiting room responsive to the scheduling system being unable to schedule the upcoming virtual appointment involving the second patient, wherein the one or more processors are configured to change the data structure to return the second patient to the virtual waiting room to change the digital display of each of the applications of the plural healthcare provider devices to change the appearance of the second patient in the virtual waiting room displayed in the applications to indicate that the second patient is available for the virtual encounter,
the one or more processors configured to establish a second wireless connection across the network between the first healthcare provider device and a second patient device of the second patient after changing the data structure to return the second patient to the virtual waiting room.

10. The telehealth system of claim 9, wherein the one or more processors are configured to change the data structure to prevent the second patient from being selected by any of the plural healthcare providers for the virtual encounter while the second patient is locked out of the virtual waiting room.

11. The telehealth system of claim 9, wherein the one or more processors are configured to change the data structure stored in the database of the telehealth system to indicate the second patient is locked out of the virtual waiting room by adding a lock flag or changing a value of the lock flag in the data structure.

12. The telehealth system of claim 11, wherein the one or more processors are configured to change the data structure stored in the database of the telehealth system to return the second patient to the virtual waiting room without the second patient losing the waiting location in the order of the virtual waiting room by removing the lock flag or changing the value of the lock flag in the data structure.

13. The telehealth system of claim 9, wherein the one or more processors are configured to change the data structure stored in the database of the telehealth system to return the second patient to the virtual waiting room without the patient losing the waiting location in the order of the virtual waiting room such that one or more prior patients that entered the virtual waiting room before the second patient are ahead of the second patient in the virtual waiting room and one or more subsequent patients that entered the virtual waiting room after the second patient are behind the second patient in the virtual waiting room.

14. The telehealth system of claim 9, wherein the one or more processors are configured to change the data structure stored in the database of the telehealth system to remove the second patient from the virtual waiting room responsive to the scheduling system successfully scheduling the upcoming virtual appointment involving the second patient.

15. A method comprising:
providing remote access of a telehealth system across a network to plural healthcare provider devices associated with plural healthcare providers to allow the plural healthcare providers to conduct a virtual encounter with several patients;
determining a threshold time period using an artificial intelligence (AI) neural network and one or more models of the AI neural network;
directing applications of the plural healthcare provider devices to notify the plural healthcare providers that one or more of the patients are available for the virtual encounter;
establishing a first wireless connection across the network between a first healthcare provider device of the plural healthcare provider devices and a first patient device of a first patient of the several patients responsive to receiving a request from the first healthcare provider device for the virtual encounter with the first patient;
examining a data structure stored in a database of the telehealth system to determine whether a second patient of the several patients having a waiting location in an order among the several patients in a virtual waiting room for the virtual encounter with a healthcare provider has been waiting at least as long as the threshold time period that was determined using the AI neural network;
responsive to determining that the second patient has been waiting for at least as long as the threshold time period, changing the data structure stored in the database of the telehealth system to indicate that the second patient is locked out of the virtual waiting room while a scheduling system of the telehealth system attempts to schedule an upcoming virtual appointment involving the second patient, wherein the second patient cannot be selected by the healthcare provider for the virtual encounter while the second patient is locked out of the virtual waiting room;
changing a digital display of the applications of the healthcare provider devices to change an appearance of the second patient in the virtual waiting room displayed in the application to indicate that the second patient is not available for the virtual encounter;
responsive to the scheduling system being unable to schedule the upcoming virtual appointment involving the second patient, providing feedback to the AI neural network and changing the data structure stored in the database of the telehealth system to return the second patient to the virtual waiting room without the second patient losing the waiting location in the order of the virtual waiting room,
wherein the data structure stored in the database of the telehealth system is changed to return the second patient to the virtual waiting room without the patient losing the waiting location in the order of the virtual waiting room such that one or more subsequent patients that entered the virtual waiting room after the second patient are behind the second patient in the virtual waiting room;
changing the digital display of the applications of the healthcare provider devices of the healthcare providers to change the appearance of the second patient in the virtual waiting room displayed in the applications to indicate that the second patient is available for the virtual encounter;
changing the one or more models of the AI neural network based on the feedback that is provided to the AI neural network;
changing the threshold time period using the AI neural network and based on the one or more models that are changed; and
establishing a second wireless connection across the network between the first healthcare provider device and a second patient device of the second patient after changing the data structure to return the second patient to the virtual waiting room.

16. The method of claim 15, wherein the data structure stored in the database of the telehealth system is changed to indicate the second patient is locked out of the virtual waiting room by adding a lock flag or changing a value of the lock flag in the data structure.

17. The method of claim 16, wherein the data structure stored in the database of the telehealth system is changed to return the second patient to the virtual waiting room without the second patient losing the waiting location in the order of the virtual waiting room by removing the lock flag or changing the value of the lock flag in the data structure.

18. The method of claim 15, wherein at least one of the subsequent patients entered the virtual waiting room while the second patient was working with the scheduling system to schedule the upcoming virtual appointment.

19. The method of claim 15, further comprising:
changing the data structure stored in the database of the telehealth system to remove the second patient from the virtual waiting room responsive to the scheduling system successfully scheduling the upcoming virtual appointment involving the second patient.

20. The method of claim 15, wherein the data structure stored in the database of the telehealth system is changed to return the second patient to the virtual waiting room without the second patient losing the waiting location in the order of the virtual waiting room such that one or more prior patients that entered the virtual waiting room before the second patient are ahead of the second patient in the virtual waiting room.

* * * * *